(12) United States Patent
Nunn

(10) Patent No.: US 7,914,986 B2
(45) Date of Patent: Mar. 29, 2011

(54) DETECTION OF AMPLICON CONTAMINATION DURING PCR EXHIBITING TWO DIFFERENT ANNEALING TEMPERATURES

(75) Inventor: Miles Andrew Nunn, Oxford (GB)

(73) Assignee: Amplion Limited, Oxford (GB)

( * ) Notice: Subject to any disclaimer, the term of this patent is extended or adjusted under 35 U.S.C. 154(b) by 919 days.

(21) Appl. No.: 11/596,703

(22) PCT Filed: May 19, 2005

(86) PCT No.: PCT/GB2005/001934
§ 371 (c)(1),
(2), (4) Date: Nov. 16, 2006

(87) PCT Pub. No.: WO2005/113803
PCT Pub. Date: Dec. 1, 2005

(65) Prior Publication Data
US 2009/0311672 A1    Dec. 17, 2009

(30) Foreign Application Priority Data
May 19, 2004  (EP) .................................. 04090202

(51) Int. Cl.
*C12Q 1/68*     (2006.01)
*C12P 19/34*    (2006.01)

(52) U.S. Cl. ........................................ 435/6; 435/91.2

(58) Field of Classification Search ............... 435/6, 91.2
See application file for complete search history.

(56) References Cited

U.S. PATENT DOCUMENTS
6,844,155 B2 *  1/2005  Shuber ............................. 435/6

FOREIGN PATENT DOCUMENTS
WO          99/20798      *  4/1999

OTHER PUBLICATIONS

Weighardt et al., PCR Methods and Applications 3, 77-80 (1993).*

* cited by examiner

*Primary Examiner* — Kenneth R. Horlick
(74) *Attorney, Agent, or Firm* — Laurence A. Greenberg; Werner H. Stemer; Ralph E. Locher

(57) ABSTRACT

A method to perform PCR reactions with one set of primers comprising sequence elements that are complementary to the target sequence and comprising sequence elements that server as tagging sequences. By conducting amplification reactions at different temperatures, the presence of contaminations arising from amplification products of previous reactions can be determined, improving reliability of the reaction and reducing the need for control reactions and reproduction of reactions.

11 Claims, 16 Drawing Sheets

NO CONTAMINATION:                      CONTAMINATION:

⇓ (1) Annealing temp.  ⇓
     72degC x 30 cycles

No                                      Product

⇓ (2) Annealing temp.  ⇓
     ≤58degC x 30 cycles

Product                                 Product

NO CONTAMINATION:　　　　　　　CONTAMINATION:

Target

Previous (1) Annealing temp. 72degC x 30 cycles

No

Product (2) Annealing temp. ≤58degC x 30 cycles

Product

Product

SEQUENCE LISTING

<160> NUMBER OF SEQ ID NOS: 3

<210> SEQ ID NO 1
<211> LENGTH: 70
<212> TYPE: DNA
<213> ORGANISM: Ebola Virus

<400> SEQUENCE: 1
agacagagta tttgttcgag gttgacaatt tgacctacgt ccaacttgaa        50
tcaagattca caccacagtt                                         70

<210> SEQ ID NO 2
<211> LENGTH: 28
<212> TYPE: DNA
<213> ORGANISM: artificial sequence
<220> FEATURE:
<223> OTHER INFORMATION: Synthetic forward primer used for
      amplification. First 10 base pairs are non-complimentary to the
      Ebola target DNA

<400> SEQUENCE: 2
gtacggatcc agacagagta tttgttcg                                28

<210> SEQ ID NO 3
<211> LENGTH: 29
<212> TYPE: DNA
<213> ORGANISM: artificial sequence
<220> FEATURE:
<223> OTHER INFORMATION: Synthetic reverse primer used for
      amplification. First 10 base pairs are non-complimentary to the
      Ebola target DNA

<400> SEQUENCE: 3
gttcgctacc aactgtggtg tgaatcttg                               29

DETECTION OF AMPLICON
CONTAMINATION DURING PCR
EXHIBITING TWO DIFFERENT ANNEALING
TEMPERATURES

FIELD OF THE INVENTION

The invention pertains to the field of molecular diagnostic methods, specifically to methods using the polymerase chain reaction. More specifically, the invention provides a method to detect the presence of amplicon contamination in a polymerase chain reaction.

BACKGROUND OF THE INVENTION

The polymerase chain reaction (PCR) is a method to selectively amplify DNA. The method uses paired sets of oligonucleotides that hybridise to opposite strands of DNA and define the limits of the sequence that is amplified. The oligonucleotides prime multiple sequential rounds of DNA synthesis catalysed by a thermostable DNA polymerase. Each round of synthesis is normally preceded by a melting and re-annealing step. The method can rapidly amplify virtually any DNA sequence (Saiki et al., Science 239:487, 1988).

PCR is widely used for the genetic identification of unique sequences in individual organisms. Uses include: forensic analysis (Gill, (2002) Biotechniques 32, 366-372), diagnosis of genetic disorders and disease susceptibility, neoplastic disease (Raj, (1998) Cancer 82, 1419-1442), detection of infectious diseases (Daxboeck (2003) Clinical Microbiology and Infection 9, 263-273) and food testing (Malorne (2003) International Journal of Food Microbiology 83, 39-48). The DNA of interest is typically amplified from genomic DNA, viral DNA, or from cDNA reverse transcribed from RNA.

In common with other assays, PCR is subject to both 'false negative' and 'false positive' results. False negative results are due to reaction failure. False positive results may be caused by primers annealing to sequences other than the true recognition sequence leading to amplification of spurious products, or by primers annealing to the true recognition sequence present in contaminating DNA derived from a source other than the sample being diagnosed. True recognition sequences contained in the sample being diagnosed will be termed "target" in the following. True recognition sequences contained in contaminating DNA are not classified as target DNA.

The most frequent and potent source of contaminating DNA that causes false positives is previously amplified PCR products (termed amplicons) with recognition sequences identical to those of the primers being used (Rolfs et al., (1992) PCR: clinical diagnostics and research. Springer-Verlag, Berlin). The probability of contamination increases when diagnostic PCR is carried out many times for one DNA sequence, and when the PCR technique has been designed to detect a small number of molecules of DNA. Contamination by previous PCR products is called 'carryover' to distinguish it from contamination by DNA from other sources.

Even strict adherence to good laboratory practice and protocols that aim to avoid any contact of amplicon with pre-amplification reagents or samples cannot guarantee the absence of false positives due to amplicon contamination. As a result, a significant part of the cost of diagnostic or forensic PCR assays is caused by the need to include a relatively large number of negative controls and to repeat arrays of assays if the slightest indication of a contamination is found.

Thus, a method to individually ascertain the absence of amplicon contamination in any reaction is highly desirable.

Two approaches can be envisioned to solve the general problem posed by amplicon contamination: either the amplicon can be destroyed subsequent to its detection in order to avoid it contaminating any later reaction, or methods must be found to discriminate amplification product arising from DNA as opposed to amplicon contamination. The former idea has been implemented in the method of dUTP incorporation and subsequent destruction of the amplicon by uracil-N-glycosylase (see EP0401037 and references contained therein; Longo et al. (1990), Gene 93, 125-128), a method widely employed today. Other methods have been devised that follow similar rationales (Cimino et al. (1991), Nucleic Acids Research 19, 773-774; Walder et al. (1993), Nucleic Acids Research 21, 4339-434).

Richards (U.S. Pat. No. 5,650,302) discloses a method to incorporate restriction nuclease recognition sites into the primers in order to render amplicon contaminants un-amplifiable when digested with the correspondent nuclease prior to amplification.

Destruction of the amplicon after determination of its presence or quantity will reduce the likelihood of downstream contamination, but since the amplicon destruction itself is a process subject to possible failure, it cannot positively rule out false positive results due to amplicon contamination.

Shuber (U.S. Pat. No. 6,207,372) discloses a multiple duplex primer PCR method, where a universal primer sequence at the 5' end of various primer pairs allows for uniform amplification conditions for multiple targets.

Shuldiner (WO9115601) discloses a method by which RT-PCR-reactions, where the first step is elongation of a DNA primer on a RNA template, can be made more specific over a background of possible DNA contaminant sequences. This method employs two primers, one of which is a hybrid sequence comprising a target-RNA-specific sequence tract and a tagging-tract. Discrimination is achieved between target RNA and possible contaminating genomic or plasmid DNA on the basis of the different hybridization temperatures of DNA-DNA versus RNA-DNA duplexes. Since RNA-DNA-double strands are more stable and hence, have a higher melting or annealing temperature than DNA-DNA double strands, a reaction temperature can be selected at which the target-specific primer part will only anneal to a RNA target. Subsequent duplication of this first DNA transcript generated from the hybrid primer will result in a DNA strand that is elongated at its 3' end with the complementary tagging sequence, to which the hybrid primer will anneal in all subsequent amplification steps at the elevated temperature. This means that the method disclosed in WO9115601 cannot discriminate between, or exclude from being amplified, DNA amplicon produced in a previous reaction using the same primer set, although it may be a useful tool to exclude amplification from genomic DNA contaminations.

In parallel to any efforts to reduce the occurrence of contamination, it is desired to be able to discern amplification product arising from target sequences in the sample (the true positive result) and the false positive result arising from amplicon contamination.

Shuber (WO 9920798) has disclosed a method to detect contamination by amplicon sequences that relies on the use of two different oligonucleotide primer sets in two different amplification reactions. A first set of primers comprising a target-detection sequence and a contamination-detection-sequence, which is added to the 5' end of the primers, are employed to detect the presence of target sequence in the original sample, a reaction that is termed "first amplification reaction". In a second reaction mixture, a second set of primers comprising only the contamination detection sequence, are used on the original sample, in order to detect contamination of the sample by amplicon molecules produced in previous reactions.

The method disclosed in WO 9920798 achieves detection of amplicon contamination in the original sample, however it does not rule out positively the presence of amplicon contamination in any step that may be specific for the "first" (according to the terminology of WO 9920798) amplification reaction. As one example, the two reactions differ in the primers employed, and thus any amplicon contamination in the solution containing the oligonucleotide primers for the first reaction would not be detected.

Another aspect of the disclosure of WO 9920798 that may be improved upon is the use of two reaction vessels. Although tolerable in some instances, the doubling of the expense in time and material both for the reaction preparation and reagents may offset the advantage in savings from reducing false positives. A method that enables the discrimination of true and false positives without the expense of having to conduct two separate reactions would thus be highly desirable.

SUMMARY OF THE INVENTION

In view of this state of the art, it is the object of the present invention to provide a method and suitable oligonucleotide primers in order to enable amplification reactions that will discriminate between amplification signals arising from target sequences contained in the sample (true positives) and amplification signals arising from contamination by amplicon products produced in previous amplification reactions.

Accordingly the invention provides a method to amplify nucleic acid sequence, comprising the steps of selecting a forward primer comprising a complementary sequence element B that is complementary to a sequence element on said nucleic acid sequence and hybridizes to said nucleic acid sequence, and said forward primer comprising a sequence element A that is not complementary to said nucleic acid sequence and situated upstream of the said complementary primer sequence element, the difference between the annealing temperatures on their respective complementary DNA sequences of the B element and the A and B element together, respectively, being greater than 5 degree Celsius, and typically selecting a reverse primer comprising a complementary sequence element B that is reverse complementary to a different sequence element downstream on said nucleic acid sequence than the forward primer and hybridizes to the complementary strand of said nucleic acid sequence, and said reverse primer comprising a sequence element A that is not complementary to said nucleic acid sequence and situated upstream of the said complementary primer sequence element, the difference between the annealing temperatures on their respective complementary DNA sequences of the B element and the A and B element together, respectively, being greater than 5 degree Celsius, and conducting a contamination detection phase of reaction comprising one or several annealing steps followed by one or several polymerisation steps, where the forward and reverse primers are brought into contact with the DNA that is to be amplified in the presence of thermostable DNA polymerase, buffer and deoxyribonucleotides, and an annealing temperature for the annealing steps is selected at which annealing temperature the A and B sequence will anneal to and form stable double helical structures with its complementary DNA sequence but the B sequence element alone will not anneal and form stable double helical structures with its complementary sequence, and conducting a target amplification phase of reaction comprising one or several annealing steps followed by one or several polymerisation steps, where the forward and reverse primers are brought into contact with the DNA that is to be amplified in the presence of thermostable DNA polymerase, buffer and deoxynucleotides, and an annealing temperature for the annealing steps is selected at which annealing temperature the B sequence element alone will anneal and form stable double helical structures with its complementary sequence, and determining the absence or presence of a contamination with amplicon from previous polymerase chain amplification reactions with similiar primers by the absence or presence, respectively, of amplification product after the contamination detection phase of reaction.

DETAILED DESCRIPTION OF THE INVENTION

According to the present invention, PCR reactions are performed using a forward primer and a reverse primer for amplification of the target sequence, both primers comprising a target-specific sequence element B on their 3'-end, and a non-target-specific amplicon-specific tag sequence A on their 5' end. The full primer sequence will be contained in and hybridize to all amplicon products resulting from the use of these primers in previous reactions, but only the target-specific 3' sequence tracts will be contained in and hybridize to original sample target sequences.

Due to the difference in length of hybridisable sequence tract, the primers will differ in annealing temperatures on amplicon contamination and true sample target, the latter annealing temperature being substantially lower. According to the present invention, the primer pair containing A and B sequence elements as defined above, is used on the sample, together with all other ingredients normally present in a PCR reaction, most prominently heat-stable polymerase, reaction buffer and deoxyribonucleotides. The PCR reaction is then conducted for several cycles at an elevated temperature, at which the AB primers will only anneal to contamination due to previous PCR products (amplicons), and for several cycles at a lower temperature, at which the B sequence of the primers can anneal to target sequences contained in the sample.

The method of the invention may be performed using any suitable PCR machine (a thermal cycler). The apparatus which is used to perform the method may also be able to monitor the production of amplified product in the contamination detection phase of the reaction and/or the target amplification phase of the reaction. Detection of amplified product may be done by any suitable means, but is preferably done by fluorescence. One or more detections may be carried out during the method, and generally at least one detection is carried out after the contamination detection phase of the reaction and one detection after the target amplification phase of the reaction.

The inventive method is preferably performed in a real time PCR machine so that product can be detected by fluorescence throughout the reaction. For example, the first 30 cycles are performed at an annealing temperature of 72 deg C. and the second set of cycles at <58 deg C. Generally at least 10 cycles, for example at least 15, 20, 25 or more cycles are performed at the lower annealing temperature, and generally at least 15, 20, 25 or more cycles are performed at the higher temperature.

If the PCR reaction mix is contaminated with previously tagged amplicon(s) a product is obtained after the first 30 cycles at an annealing temperature of 72 deg C.

In a preferred embodiment, methods of the invention comprise the utilisation of optimal primer construction for PCR and a single PCR amplification reaction performed first at a higher and then at a lower annealing temperature. Accordingly in a highly preferred embodiment the method uses two chimeric primers that have a 3' B region that has substantial sequence similarity and is complementary to target DNA and a 5' A region(s), or tag(s), that is unrelated to and non-complementary to the target DNA. The primers are designed such that amplification of target DNA will occur at the lower annealing temperature but not at the higher annealing temperature, whereas the product generated at the lower annealing temperature will be amplified at the higher annealing temperature. PCR amplification is then performed in a single closed reaction vessel first at a higher and then at a lower annealing temperature. It is preferred that the higher and the lower annealing temperatures differ by at least 5 degrees Celsius, for example by at least 8, 10, 12 or more degrees Celsius.

Since amplification at the higher annealing temperature is typically performed before amplification at the lower annealing temperature, the presence of product after high temperature annealing amplification indicates the PCR was contaminated with previously amplified product (carryover contamination), and the results should be discarded. A lack of amplified product after high temperature annealing amplification indicates the PCR was not contaminated with previously amplified product. Presence of PCR product following the low temperature annealing but not high temperature annealing cycles indicates a positive result for the sample that is not due to carryover contamination.

The 5' A, or tag, region non-complementary to the target DNA may be any sequence (irrespective of length) that does not hybridise to a given target DNA sequence under stringent conditions (conditions that remove all primer DNA except that bound by specific complementary base pairing to a substantial length of DNA sequence).

A variant of the preferred embodiment uses one chimeric primer and one non-chimeric primer completely complementary to target DNA throughout its length. As before the chimeric primer is designed such that the melting temperature of a hybrid between the 3' B region and its complement on target DNA is lower than the melting temperature of a hybrid between the full length chimeric primer and its complement. The non-chimeric primer has a melting temperature between itself and its complement on target DNA that is higher (preferably by an amount of 5 deg Celsius or more) than the melting temperature of a hybrid between the 3' B region of the chimeric primer and its complement. Amplification with the primers for a number of cycles is undertaken first at a higher and then at a lower annealing temperature.

A further variant of the preferred embodiment uses two chimeric primers and two additional primers that are complementary to the 5'A region(s), or tag(s), of the chimeric primers. The chimeric primers comprise a 3'B region that has substantial sequence similarity and is complementary to target DNA and a 5'A region (or tag) that is unrelated to and non-complementary to the target DNA. The primers are designed such that the melting temperature of a hybrid between the 3' B region and its complement on target DNA is lower (preferably by an amount of 5 deg Celsius or more) than the melting temperature of a hybrid between the 5'A region(s) and its complementary sequence. Amplification with the four primers is undertaken first at a higher and then at a lower annealing temperature, the difference between the two annealing temperatures being greater than or equal to 5 degree Celsius. At the lower annealing temperature hybridisation between the target DNA specific 3' A regions of the primers and the target DNA generates amplified product. The product of this reaction incorporates the full-length chimeric primers (AB) including the non-complementary 5' A tag. At the higher annealing temperature, hybridisation of the 2 chimeric primers and the 2 primers complementary to the 5'A region(s) of the chimeric primers and consequent DNA amplification will only occur if previously formed product incorporating the chimeric primers is present. Since amplification at the higher annealing temperature is performed before amplification at the lower annealing temperature, the presence of product after the high temperature annealing amplification cycles indicates the PCR was contaminated with previously amplified product (carryover contamination).

A further variant of the preferred embodiment uses two chimeric primers and one additional primer complementary to the 5'A region of one of the chimeric primers. The chimeric primers comprise a 3'B region that has substantial sequence similarity and is complementary to target DNA and a 5'A region (or tag) that is unrelated to and non-complementary to the target DNA. One chimeric primer is designed such that the melting temperature of a hybrid between the 3' B region and its complement on target DNA is greater than or equal to 5 degree C. less than the melting temperature of a hybrid between the 5'A region(s) and its complementary sequence. The other chimeric primer is designed such that the melting temperature of a hybrid between the 3' B region and its complement on target DNA is greater than or equal to 5 degree Celsius less than the melting temperature of a hybrid between the full length chimeric primer and its complement. Amplification with the three primers is undertaken first at a higher and then at a lower annealing temperature, the difference between the two annealing temperatures being greater than or equal to 5 degree Celsius. The reaction and interpretation of product formation is analogous to the one outlined in the preceding alternative.

In each of the aforementioned embodiments the number of cycles at the different annealing temperatures may vary and will require optimisation for individual assays. For example a few amplification cycles at the higher annealing temperature followed by 25 cycles at the lower annealing temperature may permit discrimination between true positives and false positives due to carryover contamination.

If the maximum concentration of target DNA and minimum number of PCR cycles (e.g. 15) needed to observe it by real time PCR were known, amplification cycles at the higher temperature could be undertaken to a point at which, when lower temperature amplification began, if product is observed after fewer cycles (eg in this case 10 cycles) this could only be due to amplicon contamination.

Both primer annealing temperatures and the number of of high and low temperature cycles will require optimisation for individual assays. More than two different annealing temperatures may be used in a given reaction. Generally a single high annealing temperature and a single low annealing temperature will be used, but methods in which different high annealing temperatures and different low annealing temperatures are used are included in the invention.

Methods of the invention comprise PCR primers that have a 5' A region, or tag, non-complementary to the target DNA that may be any sequence (irrespective of length) that typically does not hybridise to a given target DNA sequence under stringent conditions (for example conditions such as 0.03M sodium chloride and 0.003M sodium citrate at from about 50° C. to about 60° C.).

The 3' B region of the primers must hybridise to the target DNA under stringent conditions (such as the stringent conditions mentioned above) but does not need to be an exact match to the target sequence. The 5'A non-complementary regions, of the chimeric forward and reverse primers may be identical or different.

In a preferred embodiment the amplification reaction is either PCR, reverse transcriptase PCR or qPCR (quantitative PCR) or chip based PCR (see below). The sample containing nucleic acid (such as DNA) to be amplified can be from any source containing biological material. The method may be particularly useful in the context of multiplex PCR, as appropriately designed tags may help normalise the amplification of multiple DNA targets (U.S. Pat. No. 6,207,372).

In another preferred embodiment, the method according to the invention is performed conducting a low temperature and the high temperature reaction simultaneously. Conventional PCR machines only allow one temperature being selected for a reaction vessel at any one time, so the reaction would have to be performed in two different vessels, which is one possible embodiment of the present invention. With the arrival of chip-based micro-fluidics technologies, it would be possible to design a reaction chamber that allows two reactions from the same PCR reaction mix on the same sample to be conducted at two different temperatures, simultaneously.

In conventional high throughput PCR the likelihood of detecting sporadic carryover contamination depends on the proportion of negative controls included. In the method of the invention every sample acts as a negative control for carryover contamination. Therefore the present invention will enable monitoring of the frequency of carryover contamination and permit appropriate remedial action to taken to reduce such contamination. It will also enable facile identification of which component of the PCR is contaminated with previous amplicons.

The invention is compatible with other PCR technologies including, but not exclusively: nested PCR, multiplex PCR, hot start PCR, touchdown PCR, mimic templates, dUTP/UNG, molecular beacons/LUX fluorogenic primers, microfluidic chip based devices for PCR, and ELISA PCR. Furthermore, unlike other methods to control amplicon contamination the invention works effectively regardless of G+C content or amplicon length, and does not modify the DNA in such a way that it is incompatible with downstream applications such as cloning or sequencing.

Additional embodiments use primers that hybridise to the 5'A tag regions or include some sequence that matches the 3'B region and target DNA.

The primers used in the present invention could be chemically modified by means well known to those skilled in the art, including but not exclusively by (i) conjugation to a label or other moiety, such fluorophores, biotin, enzymes, a quencher, digoxigenin, proteins such as minor groove binders etc., (ii) introduction of non-standard DNA bases e.g. a 3' terminal ribose residue or dUTP. The primers may comprise (preferably within the A element sequence) a restriction endonuclease site or a promoter, such as T7 promoter.

In a preferred embodiment the primers used in the method lack self complementarity and/or complementarity with any other primer present in the reaction mixture.

Samples and Targets

The present invention is suitable for use with any samples that may contain a particular target DNA molecule (which may be a predetermined target), in particular biomedical samples. The sample upon which the method is performed may comprise less than 100 copies, such as less than 50 or less than 20 copies of the DNA to be amplified (i.e. the non-amplicon DNA).

The methods of the invention are especially suitable for high throughput applications and diagnostic kits, including but not exclusively, for inherited diseases, infectious diseases, and clinical assays e,g for cancer detection. Thus the method may be used in detection of infectious agents, genetic screening, forensics, paternity testing, food safety, agri-diagnostics and veterinary medicine.

The sample upon which the method is performed is typically from an organism (e.g. a disease causing organism), such as a virus, eukaryote, prokaryote, plant, animal, bird, mammal or human. The sample typically comprises a body fluid or part of an organism. The sample may be a blood, urine, saliva, bone, semen, skin, cheek cell or hair root sample. The sample may be a food sample. The sample is typically processed before the method is carried out, for example DNA extraction may be carried out. The polynucleotide in the sample may be cleaved either physically or chemically (e.g. using a suitable enzyme).

In a preferred embodiment the sample contains human DNA, and the method is used to amplify a human gene.

The gene which is amplified may cause, predispose, or protect from specific diseases, such as BRCA (cancer), p53 and kRAS (many other cancers) or factor H (age related macular degeneration).

In one embodiment the amount of target nucleic acid present before amplification is performed is determined.

The method may be used to amplify genes from the following organisms (for example for the purpose of detecting the presence of the organisms): *tuberculosis, menigococcus, streptococcus, staphylococcus, ghonorrhoea, chlamydia, listeria, mycoplasma, E. coli* 157, *campylobacter*, HIV, HBV (hepatitis B virus), HCV (hepatitis B virus), HPV (human papilloma viruses), parvovirus B19, SARS or influenza.

Components Used in the Method of the Invention

The method of the invention may be performed using any suitable set of components in the PCR reaction. Thus any suitable thermostable DNA polymerase may be used for example. The PCR reaction mixture may comprise reagents which enhance accuracy or level of amplification, such as compounds which reduce primer dimer formation particularly thermostable or proof reading polymerases etc.

In one embodiment the invention also provides a method of making primers suitable for use in the method of the invention comprising synthesising forward and reverse primers as defined herein. Any suitable method of synthesis may be used.

Complementary Sequences

The use of complementary sequences is mentioned herein, such as within the element B of the primers. In such cases the sequence may be partially or fully complementary. Thus in the case of partial complementary sequences the sequence of element B is a homologue of the fully complementary sequence. The sequence typically has at least 70% homology, preferably at least 80, 90%, 95%, 97% or 99% homology, for example over a region of at least 15 or more contiguous nucleotides. The homology may be calculated on the basis of nucleotide identity (sometimes referred to as "hard homology").

For example the UWGCG Package provides the BESTFIT program which can be used to calculate homology (for example used on its default settings) (Devereux et al (1984) *Nucleic Acids Research* 12, p 387-395). The PILEUP and BLAST algorithms can be used to calculate homology or line up sequences (such as identifying equivalent or corresponding sequences (typically on their default settings), for example as described in Altschul S. F. (1993) J Mol Evol 36:290-300; Altschul, S, F et al (1990) J Mol Biol 215:403-10.

Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci. USA* 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci. USA* 90: 5873-5787. One measure of similarity provided by the BLAST algorithm is the smallest sum probability (P(N)), which provides an indication of the probability by which a match between two polynucleotide sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The homologous sequence typically differs from the fully complementary sequence by at least 1, 2, 3, 4, 5, 6 or more substitutions (mismatches).

PCR Device

The invention provides a PCR device which is designed to carry out the method of the invention. Thus the device will be able to heat the fluid in which the PCR reaction occurs to the appropriate temperatures, and in particular is designed to allow a PCR reaction(s) having different annealing temperatures. The device is a microfluidic PCR device comprising one or more chambers each capable of containing a fluid in which contamination detection reaction and/or target amplification reactions occur, the chambers being capable of changing the temperature of the fluid in the manner required for PCR to occur.

In one embodiment the device comprises two separate chambers whose temperature can be changed independently to allow PCR reactions to occur in the chambers, wherein in the first chamber the contamination detection reaction occurs, and in the second chamber the target amplification reaction occurs.

In one embodiment the device comprises a chamber that comprises a channel through which the fluid in which the PCR reaction occurs flows, the device being arranged so that the fluid flows into different zones of the device, wherein each zone is at a different temperature, thereby changing the temperature of the fluid in the manner required for the PCR reaction to occur.

The device may comprise a PCR reaction mixture in each chamber, wherein the PCR reaction mixture comprises a forward and reverse primer as defined herein, a thermostable DNA polymerise and deoxyribonucleotides.

Microfluidic PCR devices are known in the art, and preferred embodiments are described in Liao et al (2005) Biosensors and Bioelectronics 20, 1341-48, Biotechniques (2004) 37:20-21, Anal. Chem. (2004) 76: 6434-6439 and Anal. Chem. (2003) 75: 4591-4598. The PCR device may be made of a glass substrate with integrated thin-film platinum resistors as heating/sensing elements. Typically the PCR device is made using micro-electro-mechanical system (MEMS) techniques. In a preferred embodiment micro heaters and temperature sensors are located inside the reaction chamber(s).

The control system of the PCR device may be based on a programmable microprocessor, and the device may comprise a single microchip implemented with the control method and the required critical electrical components for measuring electrical signals. Thus the device may be programmed to carry out a temperature cycle as described above to allow the method of the invention to be performed.

The method of the invention may be carried out on any suitable PCR device described herein.

Detecting the Source of PCR Contamination

In one aspect the invention provides a method which can be used to detect the source of PCR contamination. This may be used in the situation where PCR amplification is being carried out in different sites (i.e. different physical locations), such as different laboratories, separated for example by more than 1 kilometre. The PCR reactions in different sites are generally amplifying the same or similar target sequences. The method is based on the fact that PCR reactions at different sites will be carried out using forward and reverse primers as described herein, but each site will use primers which have different A elements to those used at another site. Thus PCR products formed at different sites will incorporate their own unique A element sequence, and can be distinguished from PCR product formed at another site. Thus the invention provides a method of detecting the source of PCR contamination when a method of amplification as defined in the above sections is carried out in two or more different locations using primers with different A elements in each location, said method comprising determining which A element sequence is present in the PCR contamination, to thereby determine at which location the PCR contamination is from.

Typically PCR reactions may be performed at least 2, 5, 10, 20, 50 or more sites, and thus at least 2, 5, 10, 20, 50 or more different primer sets could be used.

Detection of the A element sequence is performed using any suitable technique, such as sequencing, hybridisation to specific oligonucleotide probes or by PCR (for example using primers which cause a PCR reaction to occur in the presence of a particular A element). During detection the A element is generally in single stranded form.

Kits Provided by the Invention

The invention provides a kit for carrying out the method of the invention comprising a forward and reverse primer as defined herein and optionally also comprising a thermostable DNA polymerise and/or buffer and/or deoxyribonucleotides and/or a thermal cycler. The invention also provides a kit for carrying out the above-mentioned method which allows the source of contamination to be determined comprising two or more oligonucleotides, wherein each oligonucleotide is capable of hybridising to different A elements (corresponding to different sets of primers that are being used in different locations), to thereby detect the presence of the A element in the PCR contamination. The kit may comprise at least 2, 5, 10, 20, 50 or more different oligonucleotides.

The kits may additionally comprise one or more of the following: a means to detect the binding of an oligonucleotide to element A, a detectable label (such as a fluorescent label), an enzyme able to act on a polynucleotide (typically a polymerase, restriction enzyme, ligase, RNAse H or an enzyme which can attach a label to a polynucleotide), suitable buffer(s) (aqueous solutions) for PCR reactions or enzyme reagents, a positive and/or negative control, a means to isolate DNA from sample, a means to obtain a sample from an organism (such as swab or an instrument comprising a needle) and a support comprising wells on which detection reactions can be performed.

DESCRIPTION OF THE FIGURES

TOP: Experiment A. Low Copy Number (from left):
1-3 Amplicon DNA
4-6 Amplicon and target DNA
7-9 Target DNA
10-12 NTC BOTTOM: Experiment B. High Copy Number (from Left)
1-3 Amplicon DNA
4-6 Amplicon and target DNA
7-9 Target DNA
10-12 NTC

The invention is illustrated by the following Examples.

EXAMPLE 1

Figure 1:
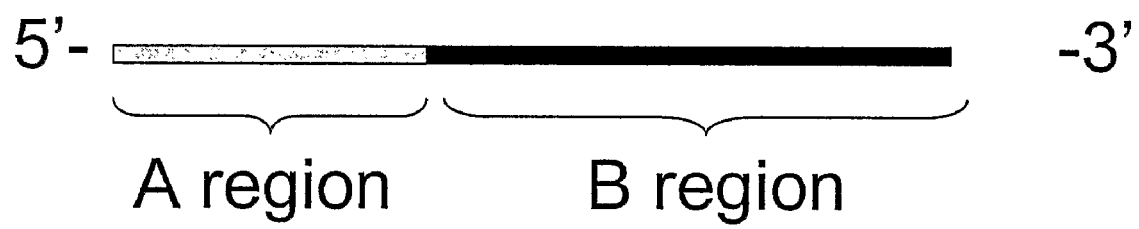
FIG. 1: Schematic representation of a chimeric primer. The B region is complementary to target DNA whereas the B region is not complementary to target DNA.
Figure 2:
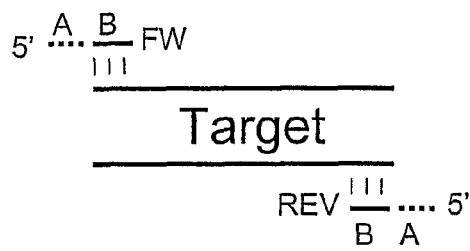
FIG. 2: Schematic representation of methodology using chimeric primers and outcome with and without carryover contamination.
Figure 2:
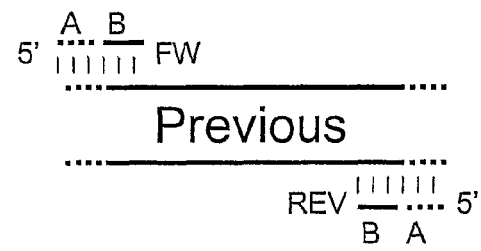
Figure 2:
Figure 2:
Figure 2:
Figure 2:

1.0 Materials
1.1. Oligonucleotides
Forward (pET24 F) and reverse (pET24 R) primers were purchased from MWG Biotech AG (standard HPSF purification, 0.01 μM scale). Primer sequences are shown in F1 below and relevant properties summarised in Tables 1 and 2. The Tm values and number of complementary residues present in primers were calculated using the software available at http://www.operon.com/oligos/toolkit and the Roche LightCycler Probe Design software, version 2.0. The Tm of the 15 base pair (bp) regions complementary to target DNA were calculated to be ~42.7 deg C. and ~45.1 deg C. for the pET24 F and R primers respectively. Primer stocks were diluted to 100 μM.

F1 The primers have 21 bp 5' regions (underlined) that are not complementary to target DNA and 15 bp 3' regions (not underlined) that are complementary to target DNA.

pET24 F  5'-<u>CCG ACC CGC CAG CAG GAC CCC</u> GAT AAC AAT TCC CCT-3' pET24 R  5'-<u>CCG CCA GGA CCC CAG CGT GCC</u> CAA AAA ACC CCT CAA-3'

TABLE 1

Properties of the single primers

| Primer | Length (bp) | Tm (deg C.) | GC content (%) | Reverse complement |
|---|---|---|---|---|
| pET24 F | 36 | ~78.1 | 63.9 | 0 consecutive; 4 total |
| pET24 R | 36 | ~78.1 | 63.9 | 0 consecutive; 0 total |

TABLE 2

Properties of the primer pair

| Primer | Length of PCR product (bp) | Reverse complementarity |
|---|---|---|
| pET24 F/pET24 R | 309 | 0 consecutive; 0 total |

1.2. Target DNA

A 5307 base pair (bp) circular expression plasmid called pET 24d(+) from Novagen (Catalogue number 69752-3) was used as the target DNA (~$5.87 \times 10^{-18}$ g/molecule). A stock solution of the plasmid was stored (−70 deg C.) at a concentration of 2.37ng/µL ($4.03 \times 10^8$ molecules/uL). The region of the plasmid DNA to which the primers anneal is shown in F2.

F2 Nucleotide sequence of pET 24d(+) in region that is amplified by PCR using the forward and reverse primers. Underlined sequences are complementary to the last 15 base pairs of the primers. The forward and reverse primers anneal either side of the pET24d(+) multicloning site which is indicated in italics. pET 24d(+) nucleotide numbering shown for first and last base in the figure.

```
347                                            FW3
TCGATCCCGCGAAATTAATACGACTCACTATAGGGGAATTGTGAGCGGATAACAATTCCCC

TCTAGAAATAATTTTGTTTAACTTTAAGAAGGAGATATACCATGGCTAGCATGACTGGTGG

ACAGCAAATGGGTCGGGATCCGAATTCGAGCTCCGTCGACAAGCTTGCGGCCGCACTCGAG

CACCACCACCACCACCACTGAGATCCGGCTGCTAACAAAGCCCGAAAGGAAGCTGAGTTGG

CTGCTGCCACCGCTGAGCAATAACTAGCATAACCCCTTGGGGCCTCTAAACGGTCTTGAGG

GGTTTTTTG
26                                                      REV3
```

1.3. Amplicon DNA

Amplicons (~$1.38 \times 10^{-19}$ g/molecule) were derived from the first PCR reactions performed on target DNA with primer pairs pET F/pET R (see below). The concentration of amplicon DNA was determined by spectrophotometry at 260 and 280 nm wavelengths and stock solutions, prepared directly from the PCR mixture, adjusted to a concentration of 6.85 ng/µL ($4.96 \times 10^{10}$ molecules/uL).

1.4. PCR Premix

Immolase 2× premix from Bioline Ltd (cat #BIO-25019) was used. The polymerase in the premix is activated by incubating it at 95 deg C. for 7 minutes.

1.5 Thermocyclers

PCR was undertaken using an MJ DNA Engine® (PTC-200™) Peltier Thermal Cycler.

2.0 Methods

2.1. PCR Mixtures

25 µL PCR mixtures contained the following:
12.5 µL Immolase 2× premix (enzyme, dNTPs, buffer mix)
2 µm pET24 F (i.e. 0.5 µL from 100 µM stock)
2 µM pET24 R After addition of amplicon/template mixtures were made up to the final volume with nuclease free water.

2.1. Thermocycling Conditions

Cycling conditions for low annealing temperature amplification of target DNA to obtain amplicon (FIG. 3) were:
Enzyme activation. 1 cycle of:
95 deg C., 7 minutes
Amplification. 28 cycles of:
95 deg C., 50 seconds
45 deg C., 30 seconds
72 deg C., 30 seconds Cycling conditions for high annealing temperature amplification of amplicon DNA (FIG. 4) were:
Enzyme activation. 1 cycle of:
95 deg C., 7 minutes
Amplification. 28 cycles of:
95 deg C., 50 seconds
72 deg C., 40 seconds Cycling conditions for amplification of amplicon and target DNA at high and then low annealing temperature (FIG. 5) were:
Enzyme activation. 1 cycle of:
95 deg C., 7 minutes
High temperature annealing amplification. 10 cycles of:
95 deg C., 50 seconds
72 deg C., 40 seconds
Low temperature annealing amplification. 28 cycles of:
95 deg C., 50 seconds
50 deg C., 30 seconds
72 deg C., 30 seconds

3.0 Results

Figure 3:
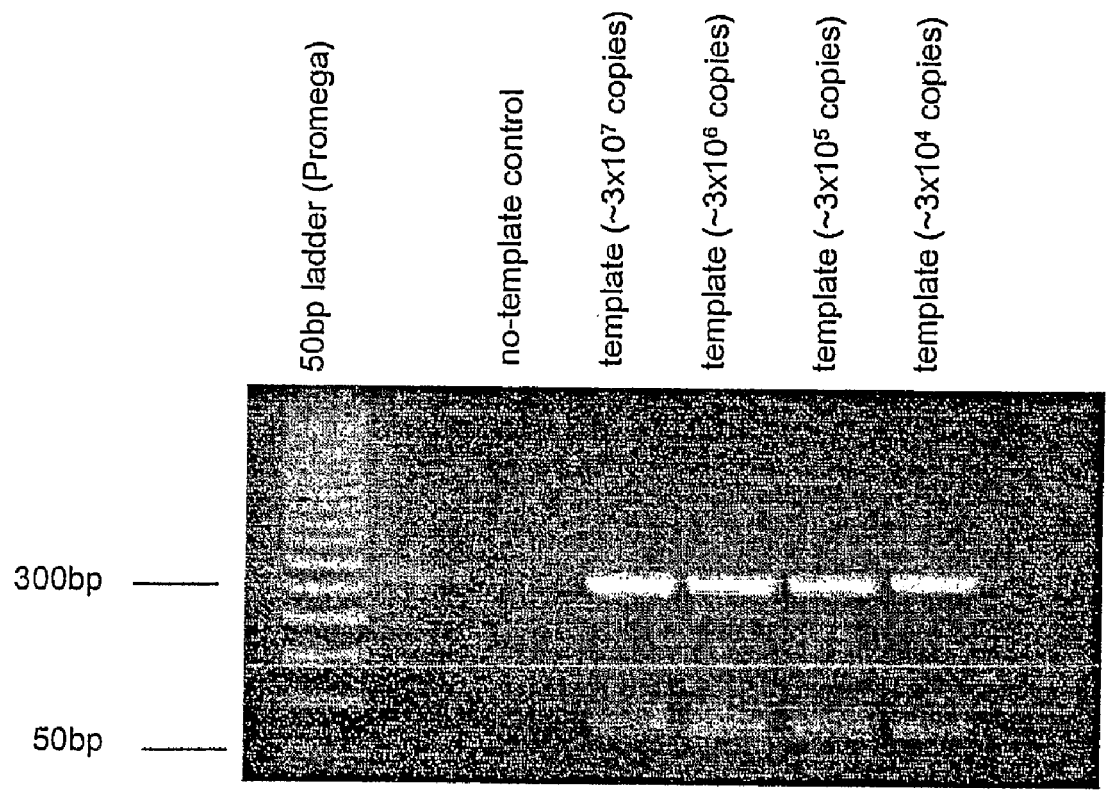
FIG. 3: Formation of amplicon from pET 24d(+) target DNA using pET F and R primers at annealing temperature of 45 deg C. 2.5% agarose gel stained with ethidium bromide. Marker sizes (base pairs) indicated on left of figure. The approximate number of copies of template DNA added to each reaction is indicated.

The first PCR performed with pET24 F and R specifically generated amplicon from target DNA (FIG. 3). Amplicon concentration was determined by spectrophotometry. Stock solutions were stored at −70 deg C. and serial dilutions of the stock used in all subsequent experiments.

Figure 4:
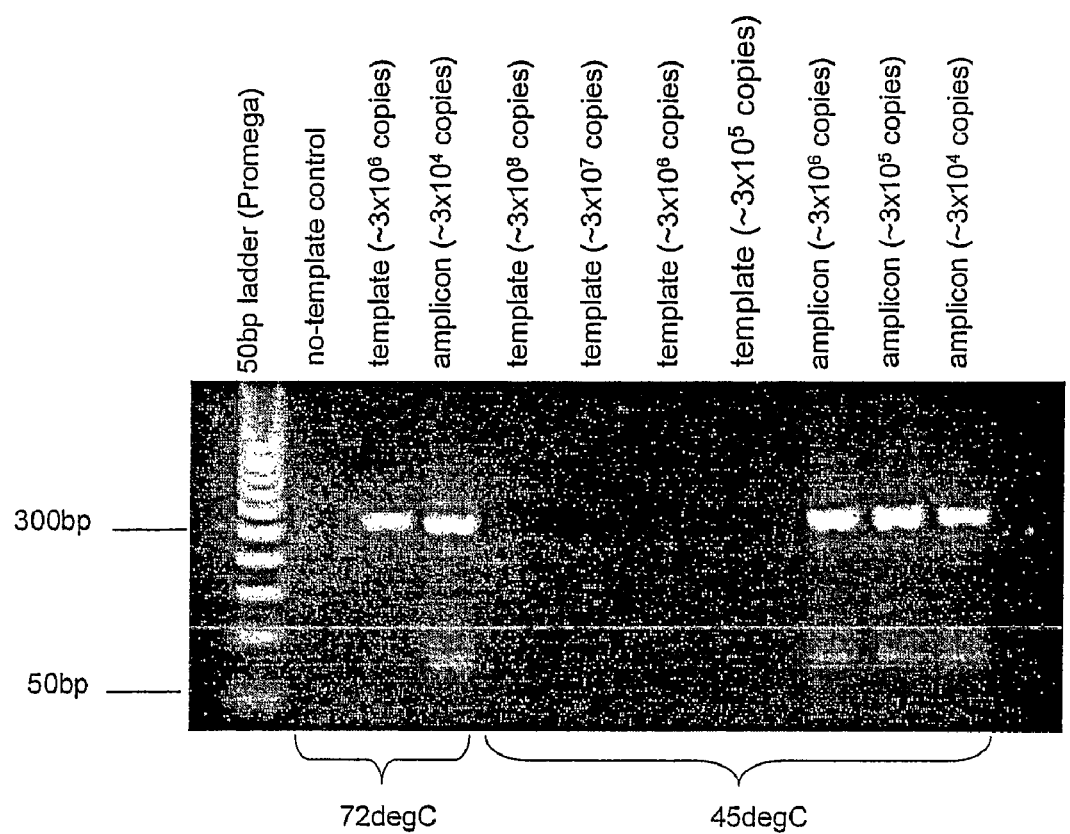
FIG. 4: Amplification of amplicon and pET 24d(+) target using pET F and R primers at annealing temperatures of 45 deg C. and 72 deg C. (as indicated below gel). Also see legend to FIG. 1.

The pET24 F and R primer pair have no bases complementary for more than two nucleotides in a row. The primers specifically amplified target DNA at annealing temperatures between 42-56 deg C. but did not amplify target DNA at annealing temperatures of ≧60 deg C. (data not shown). At an annealing temperature of 72 deg C. the primers specifically amplified amplicon but not target DNA even at high concentration (FIG. 4). The primer pair generated primer dimers in reactions performed at annealing temperatures of 72 deg C. for 30 cycles then 41 deg C. for 30 cycles (data not shown). To understand when primer dimer becomes a problem in the reactions no template controls were run for a total of 60 cycles at 45 deg C. Primer dimer only appeared after more than 45 cycles (data not shown).

Figure 5:
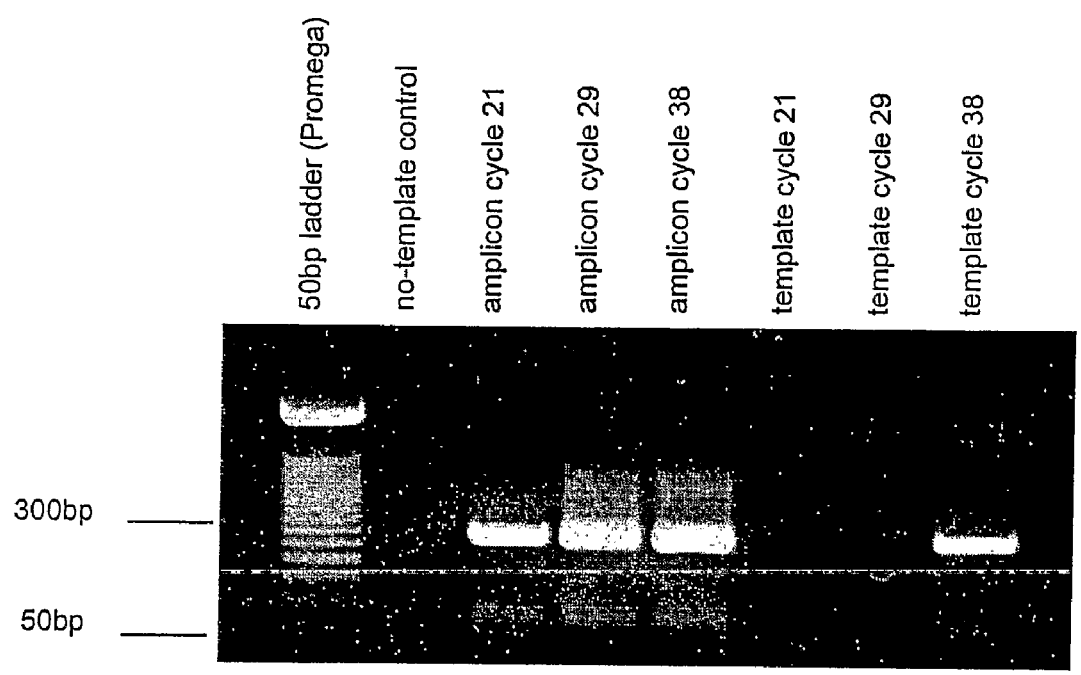
FIG. 5: Detection of amplicon (~$10^4$ copies) well before target DNA (~$3 \times 10^6$ copies) using thermocycling program comprising high and then lower temperature annealing cycles. Aliquots of the reactions were removed after 21, 29 and 38 cycles (as indicated above the gel). Also see legend to FIG. 1.
Figure 6:
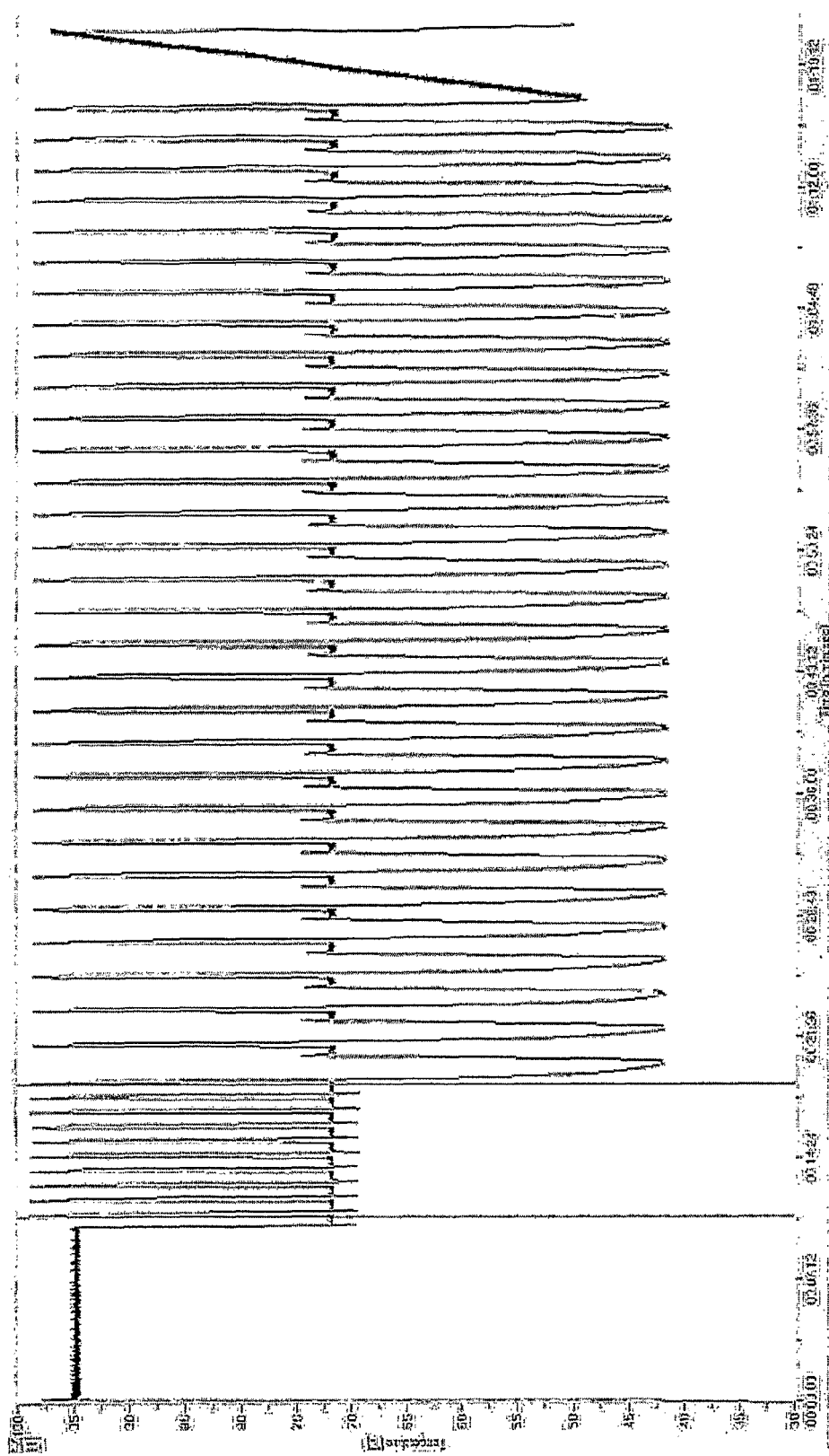
FIG. 6: Overview of Amplification Protocol for Real-time SYBR Green I 2T-TA thermal-cycling (temperature versus time). Acquisition of SYBR Green I Signal is shown. A 10 minute Taq polymerase activation step, followed by 10 cycles of High Temperature thermal cycling, followed by 45 cycles of Low Temperature Thermal Cycling, followed by a Melting curve analysis.

To keep the cycle number to a minimum reactions using FW3/REV3 were performed at an annealing temperature of 72 deg C. for 10 cycles before shifting to 52 deg C. for 28 cycles. These cycling parameters permitted specific detection of amplicon but not target DNA after 21 cycles and target DNA after 38 cycles without the formation of primer dimer (FIG. 5). Similar experiments using real-time PCR which are described in Example 2.

4.0. Conclusions

The 2T-TA methodology specifically permits detection of amplicon contamination. Tagged amplicons are amplified at the high annealing temperature (72 deg C. here) whereas target DNA is not. During the second stage of the amplification reaction the annealing temperature is dropped, primer sequences complementary to the target DNA anneal and target DNA is amplified.

The methodology is suited to a real-time PCR setting where accumulation of PCR product can be detected continuously, cycling conditions are rapid, and the primer concentrations used are low reducing rate of loss of polymerase activity and the generation rate of primer dimers.

EXAMPLE 2

Demonstration of 2T-TA Methodology Using Real Time PCR 1.0 Materials
1.1. Oligonucleotides
The forward (pET24 F) and reverse (pET24 R) primers were the same as those described in Example 1. Primer stocks were diluted to 5 μM.
1.2. Amplicon and Target DNA
Stocks of amplicon and target DNA are described in Example 1. In the real time PCR data presented in FIGS. 7 to 13 the amplicon DNA is denoted as − control, the target DNA as + control and mixtures of target and template as ±.
1.4. PCR Premix
LightCycler FastStart DNA Master SYBR Green I from Roche Applied Science (cat no. 3 003 230) was used. The polymerase in the premix is activated by incubating it at 95 deg C. for 10 minutes.
1.5 Thermocyclers
PCR was undertaken using a Roche LightCycler™.
2.0 Methods
2.1. PCR Mixtures
20 μL PCR mixtures contained the following:
2 uL LightCycler FastStart DNA Master Mix
2 mM MgCl$_2$ (per LightCycler Kit Instructions)
0.5 uM pET24 F (i.e. 2 uL from 5 uM stock)
0.5 uM pET24 R
After the addition of amplicon/target DNA mixtures were made up to the final volume with nuclease free water.
2.1. Thermocycling Conditions
Thermal cycling conditions were as follows:
Enzyme Activation: 1 cycle of:
95° C., 10 minutes, 20° C./second ramp
High temperature annealing: 10 or 30 cycles of:
95° C., 10 seconds, 20° C./second ramp
72° C., 30 seconds, 20° C./second ramp (Acquisition/cycle)
Low temperature annealing: 30 or 45 cycles of:
95° C., 10 seconds, 20° C./second ramp
42° C., 15 seconds, 20° C./second ramp
72° C., 30 seconds, 20° C./second ramp (Acquisition/cycle)
Melting Curve Analysis followed directly after amplification of template:
Melt Curve: 1 cycle of:
95° C., 10 seconds, 20° C./second ramp
50° C., 10 seconds, 20° C./second ramp (Single Acquisition)
97° C., 0 seconds, 0.2° C./second ramp (Continuous Acquisition)
3.0 Results
Experiment A: Low concentration equimolar reaction of amplicon DNA only, target DNA only and both amplicon and target DNA mixed.
~1600 copies (0.23 fg) amplicon DNA
~1200 copies (6.76 fg) target DNA Sample Set Up:

| Sample # | |
|---|---|
| 1 | Amplicon (−control) |
| 2 | Amplicon (−control) |
| 3 | Amplicon (−control) |
| 4 | Both (+/−control) |
| 5 | Both (+/−control) |
| 6 | Both (+/−control) |
| 7 | Target (+control) |
| 8 | Target (+control) |
| 9 | Target (+control) |
| 10 | NTC |
| 11 | NTC |
| 12 | NTC |

NTC: no template (water) control

Figure 7:
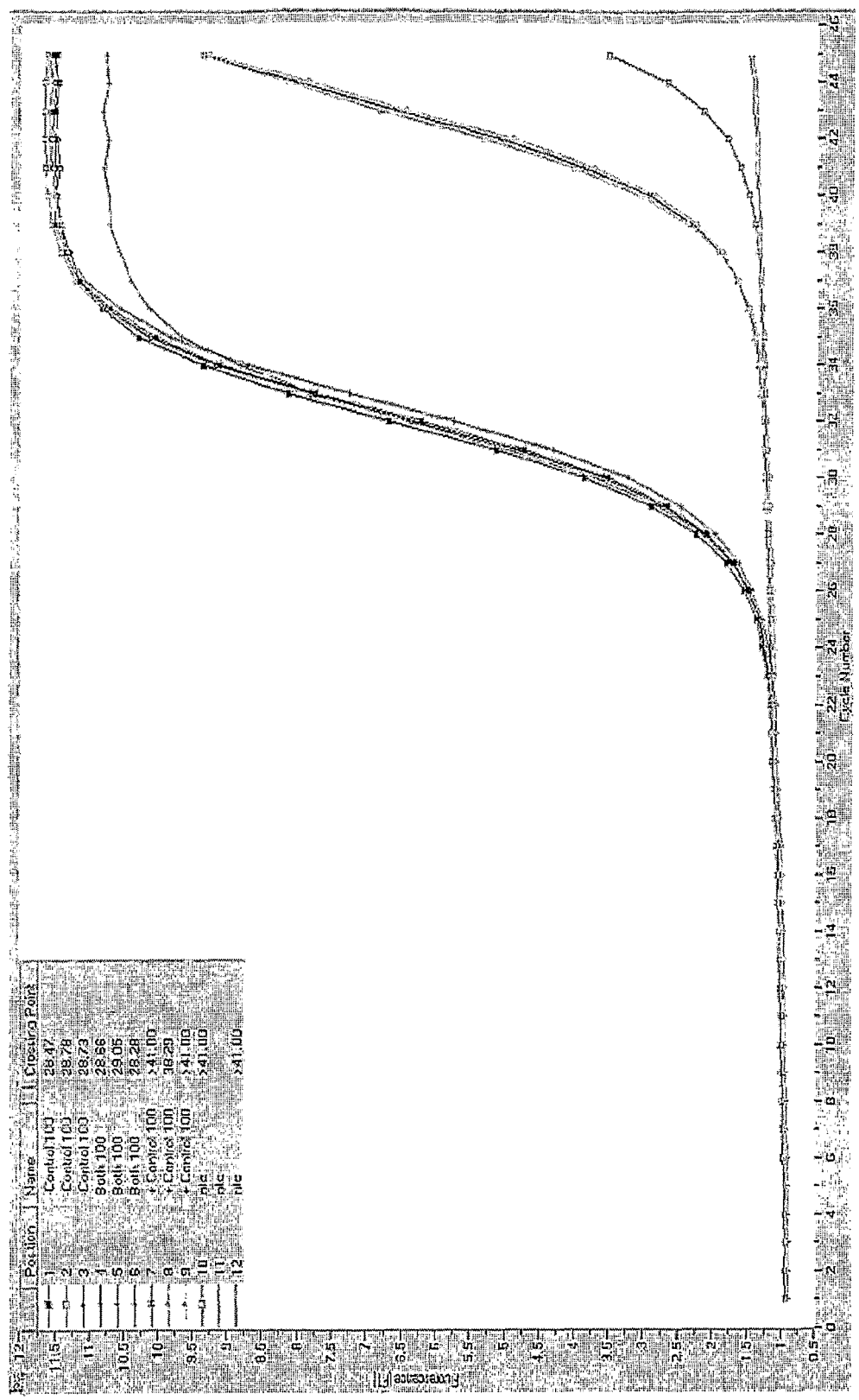
FIG. 7: Amplification with 2T-TA technique, low copy number (fluoresence versus cycles). Amplicon (~1600 copies, 0.23 fg), and target (·1200 copies, 6.76 fg). Amplicon DNA denoted as − control, target DNA as + control and mixtures of target and template as 'both'. 10 Cycles of high annealing temperature (72 deg C.) PCR was performed prior to generating this amplification data. No signal amplification was detectable during these first ten cycles which are therefore not shown in this figure.
Figure 8A:
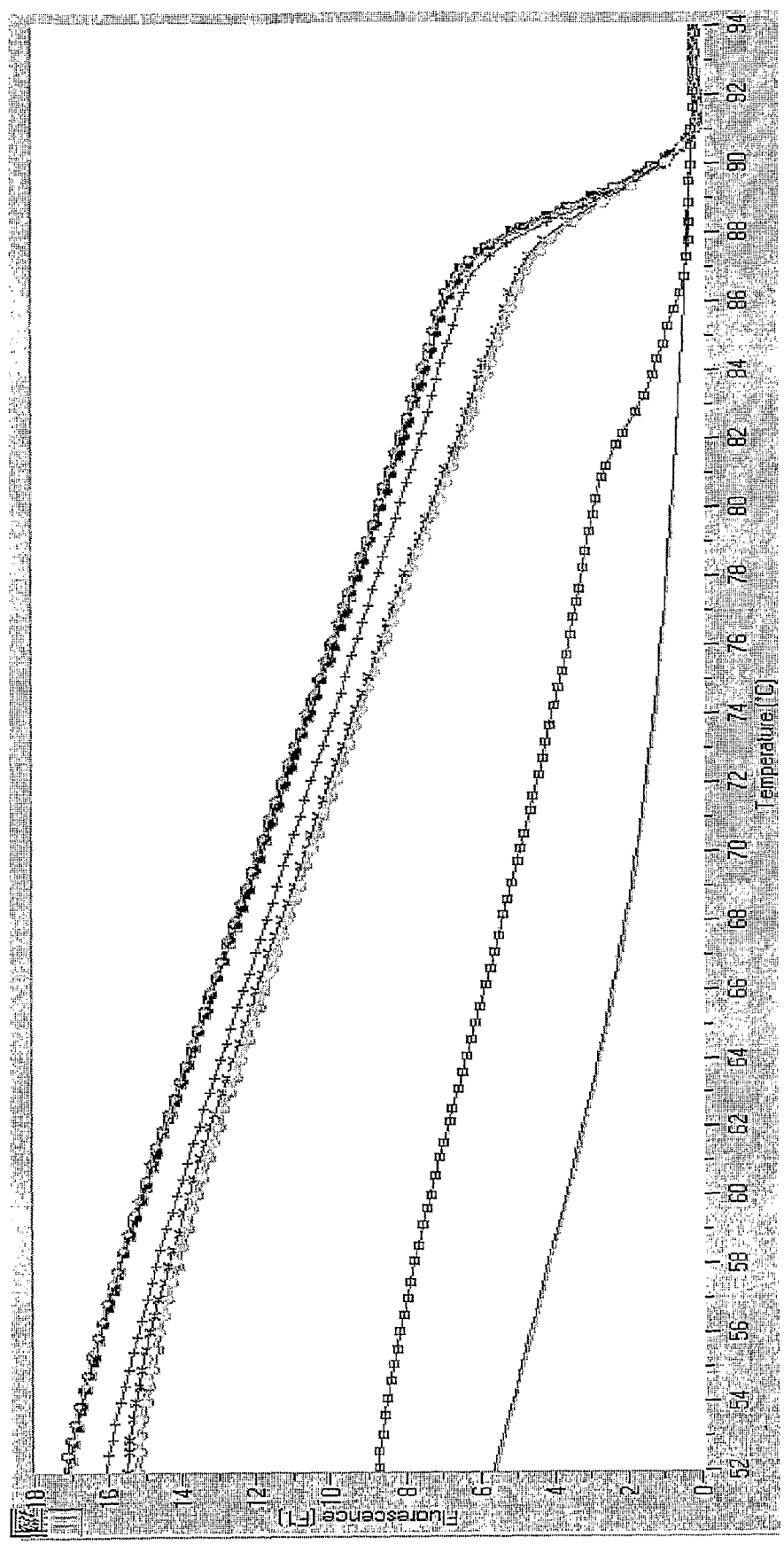
FIG. 8: Melting Curve analysis of products from 2T-TA technique using low Copy numbers of template and amplicon DNA (fluoresence versus temperature). See legend to FIG. 7 for identity of amplicon and target DNA.
Figure 8B:
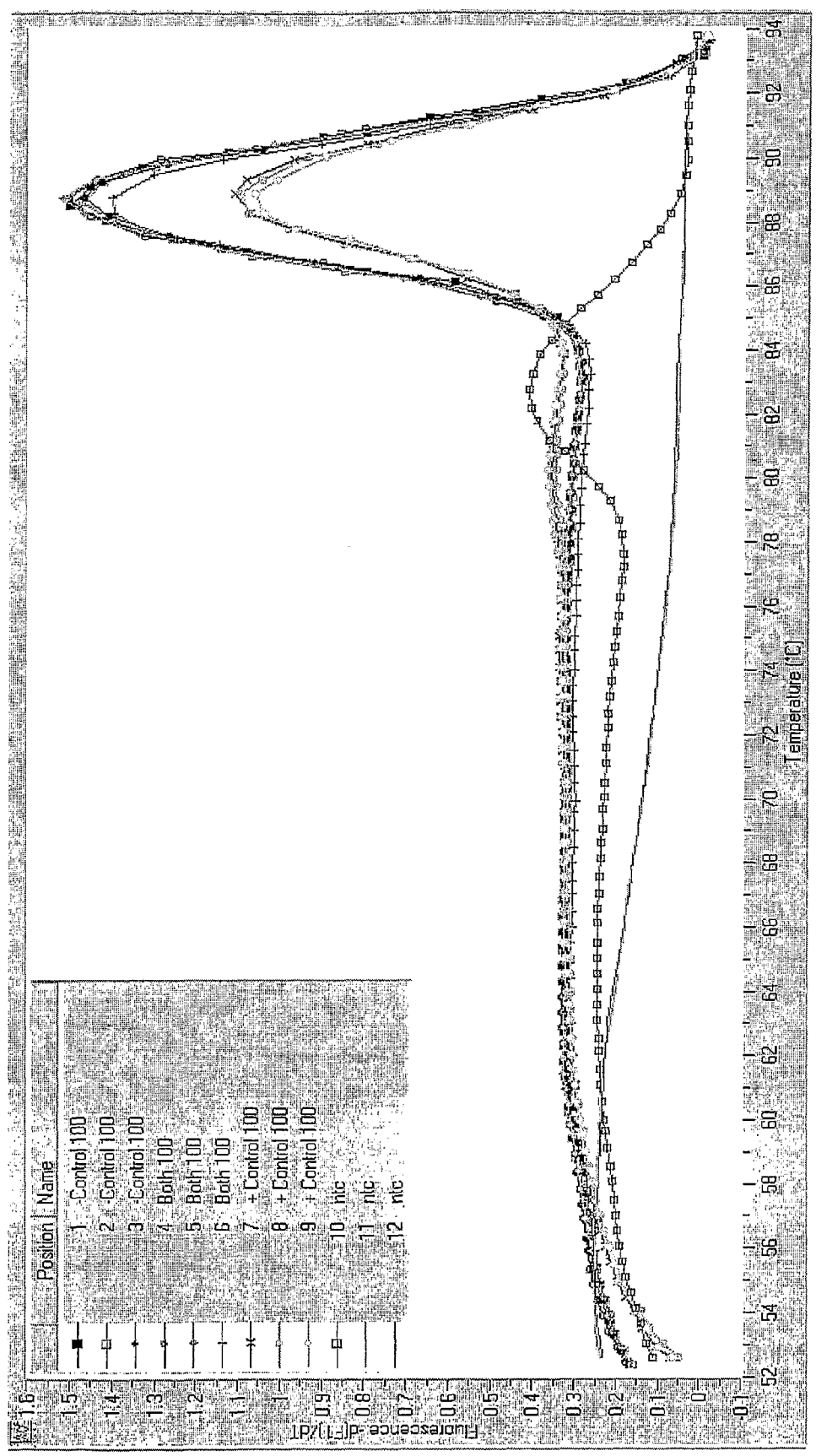
Figure 9:
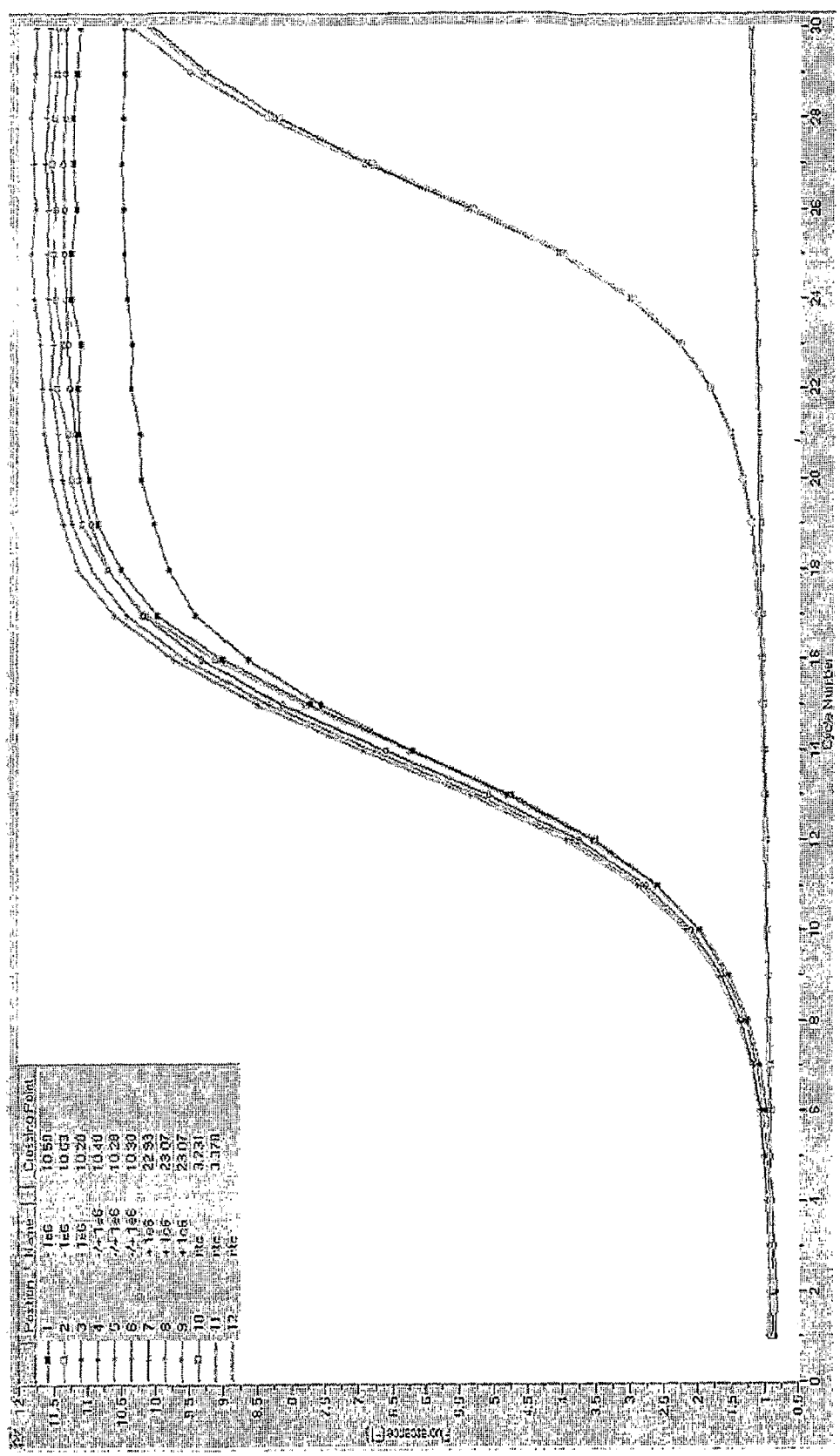
FIG. 9: Amplification with 2T-TA technique, High copy number (fluoresence versus cycles). amplicon (~$1.6 \times 10^7$ copies, 2.3 pg), and target (~$1.2 \times 10^7$ copies, 67.6 pg). Amplicon DNA denoted as − control, target DNA as + control and mixtures of target and template as +/−. 10 Cycles of the high temperature annealing PCR was performed prior to generating this amplification data. Amplicon containing samples detected 12 cycles before target DNA only samples.
Figure 10A:
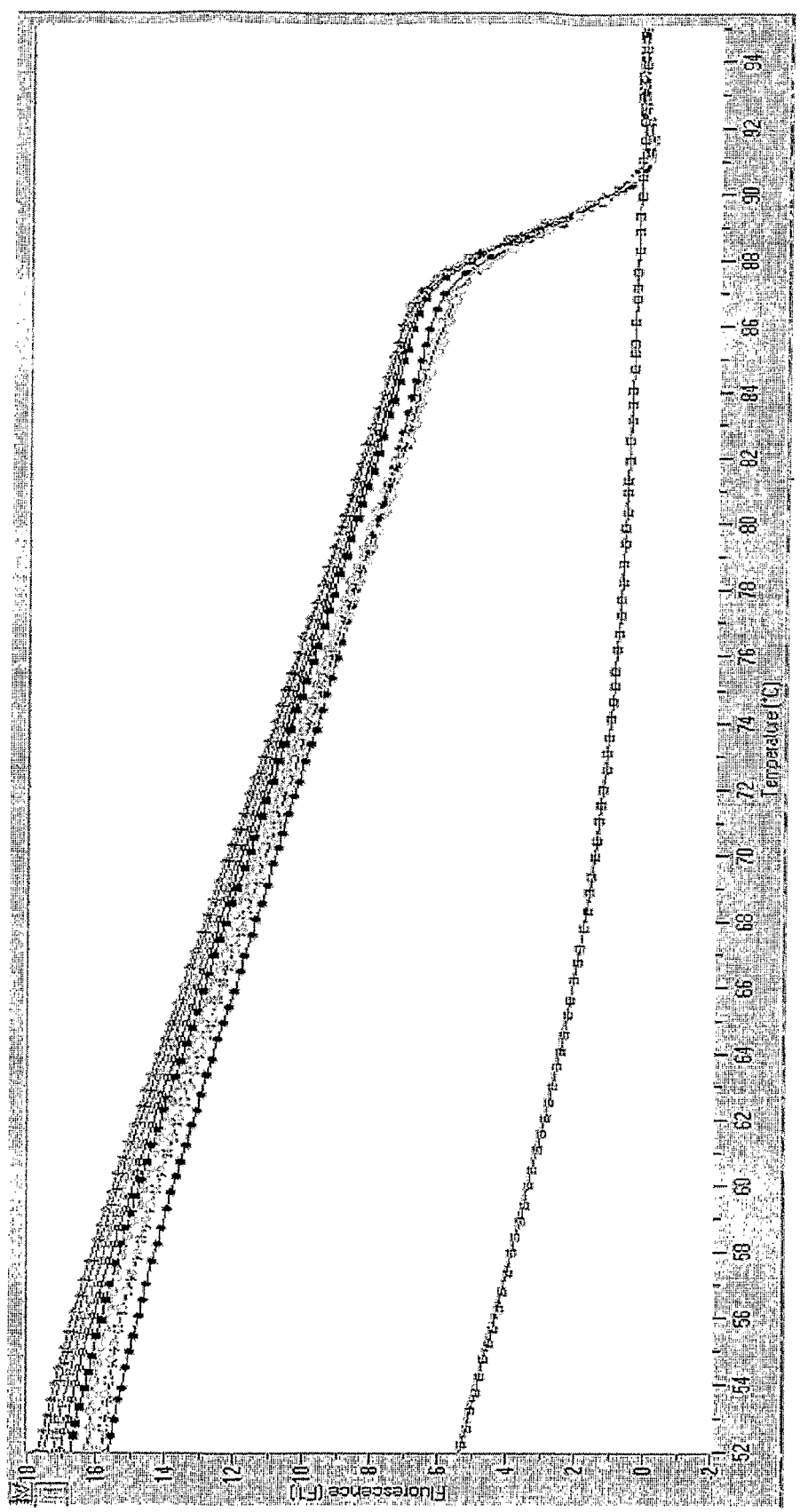
FIG. 10: Melting Curve analysis of PCR products 2T-TA technique using high copy number amplicon and target DNA (fluoresence versus temperature). See legend to FIG. 9 for identity of amplicon and target DNA.
Figure 10B:
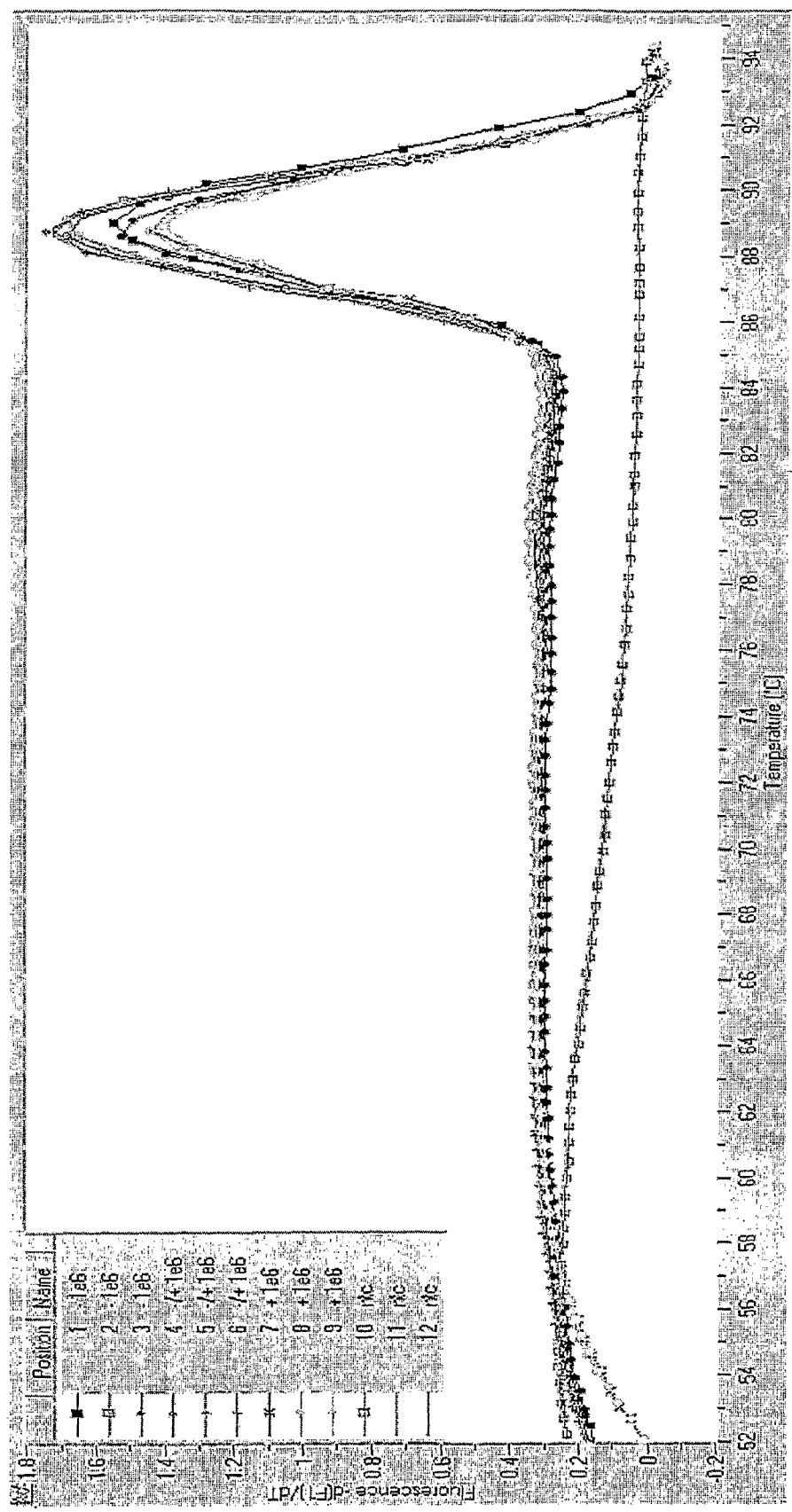
Figure 11:
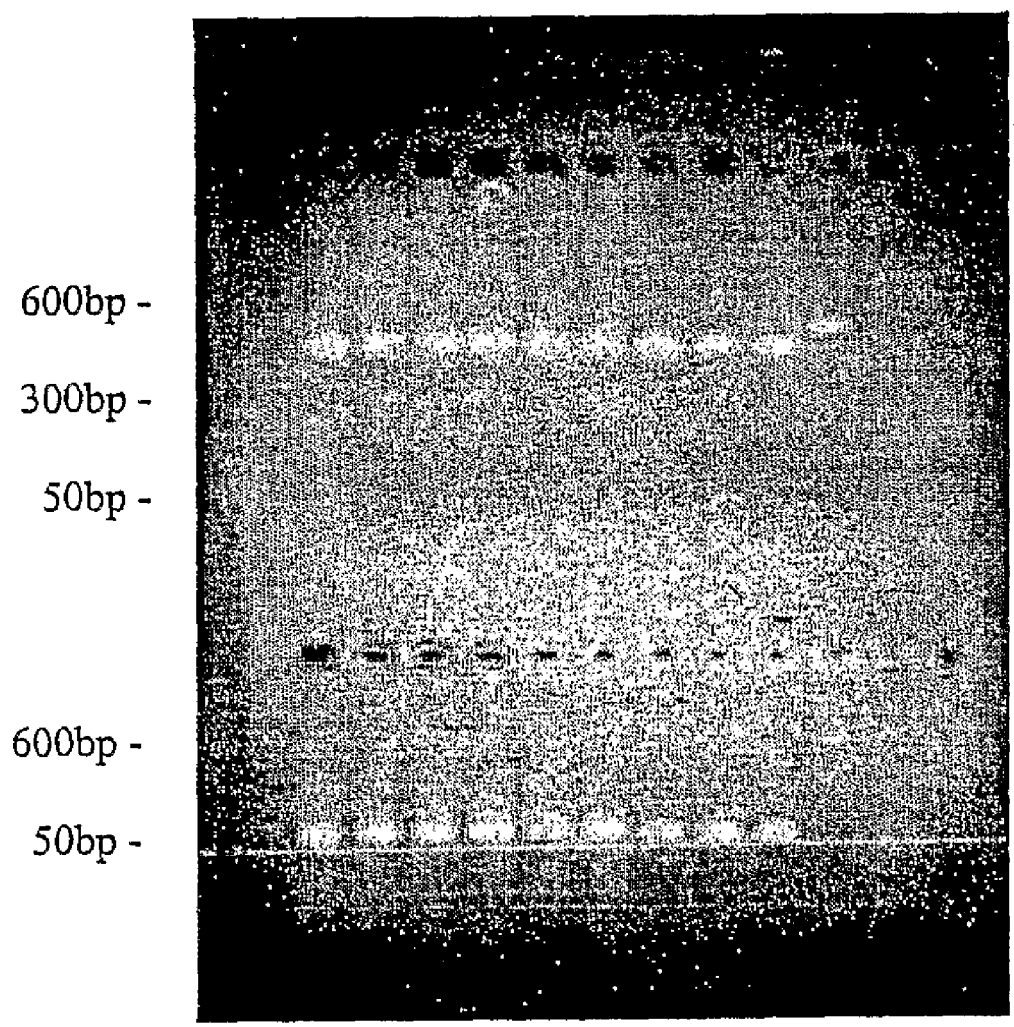
FIG. 11: 2% TBE (Agarose Gel Electrophoresis) of Amplification products from Low Copy Number and from High Copy Number amplification assays.
Figure 12:
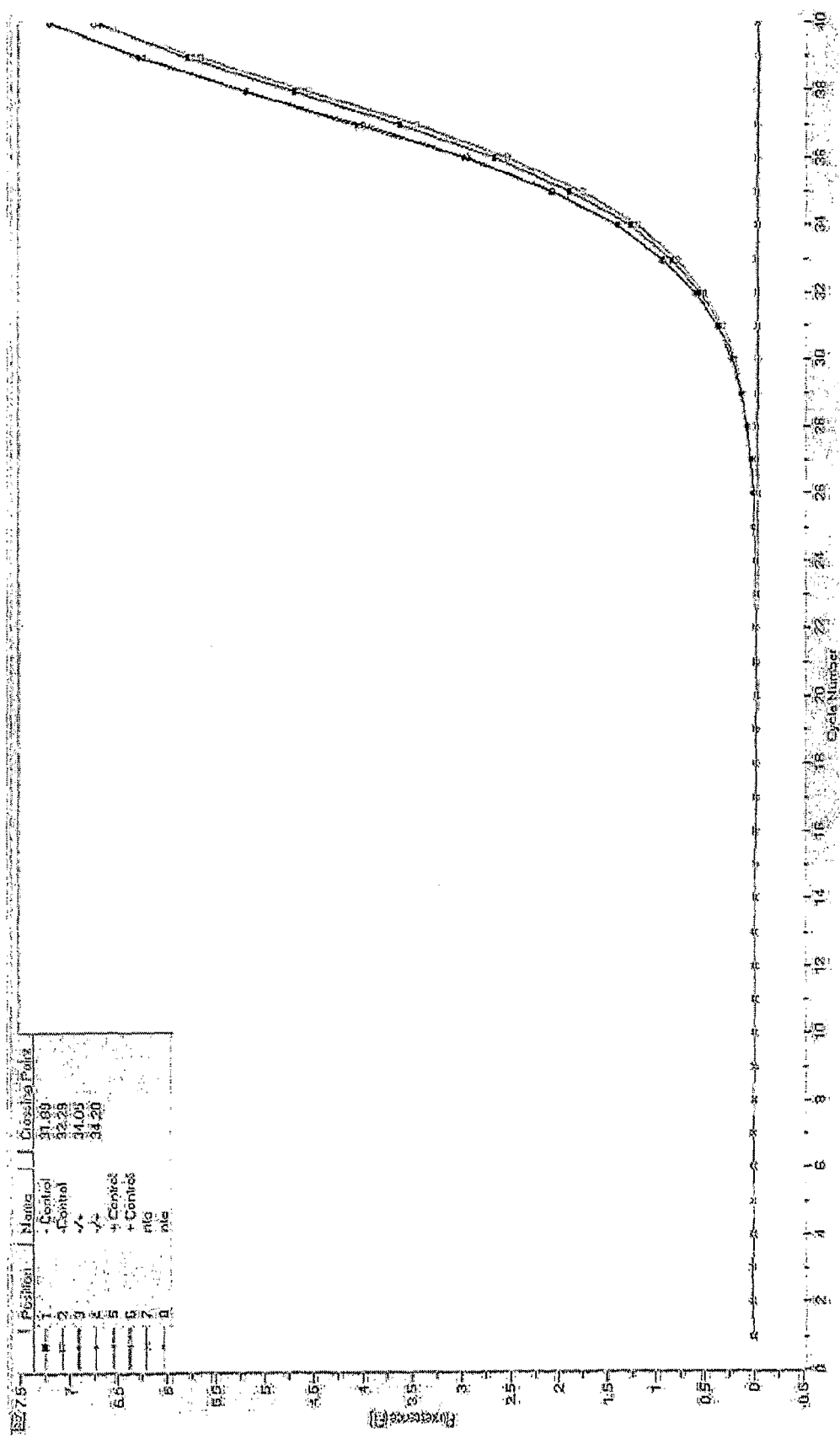
FIG. 12: High Temperature annealing cycling (fluoresence versus cycles). Only samples which contain amplicon amplify during this phase of the reaction. Amplicon DNA denoted as − control, target DNA as + control and mixtures of target and template as +/−.
Figure 13:
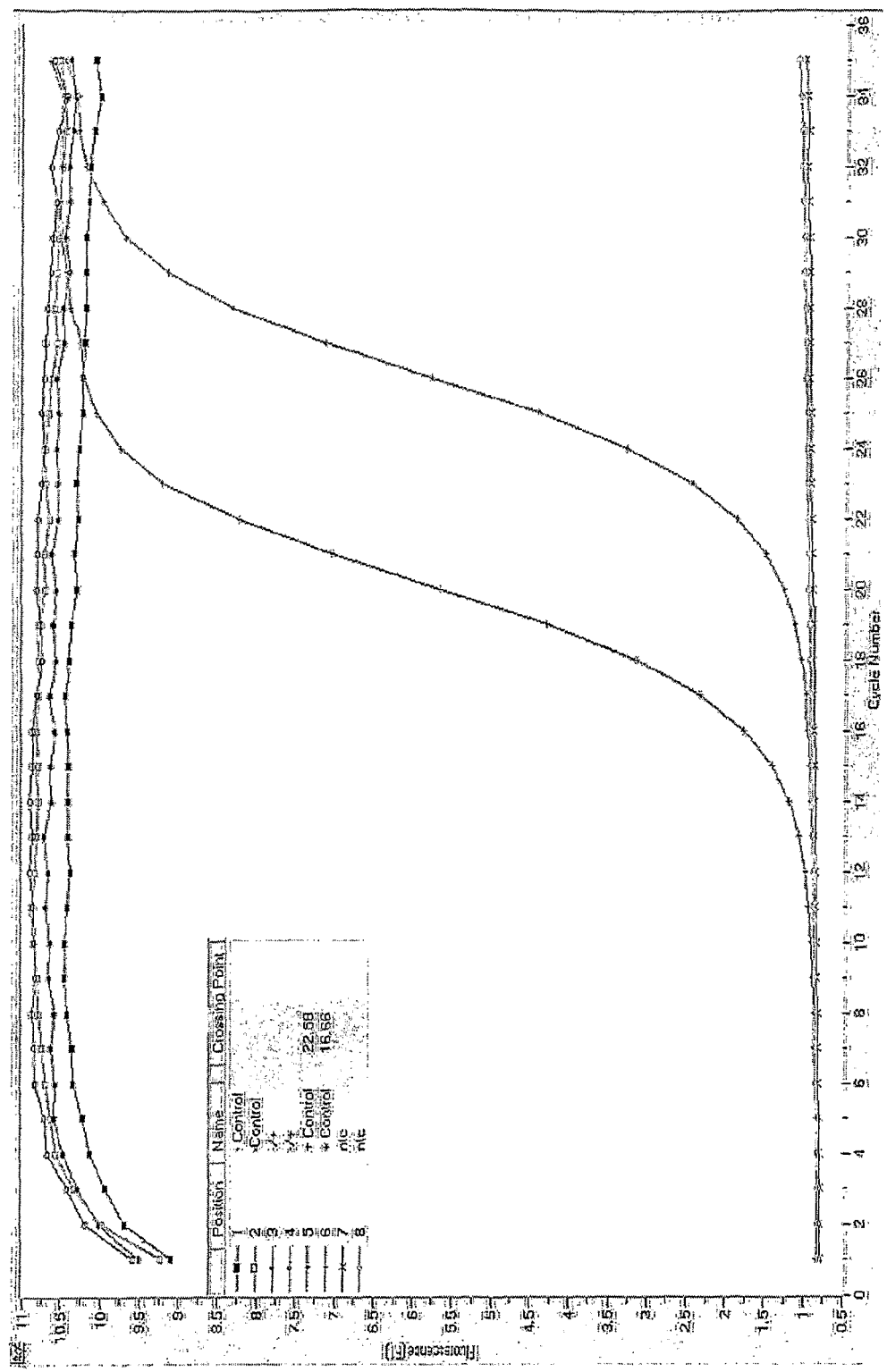
FIG. 13: Low temperature annealing cycling (fluoresence versus cycles). Reaction mixes with target DNA only amplify during this phase of the reaction. See legend to FIG. 12 for identity of amplicon and target DNA.
Figure 14:
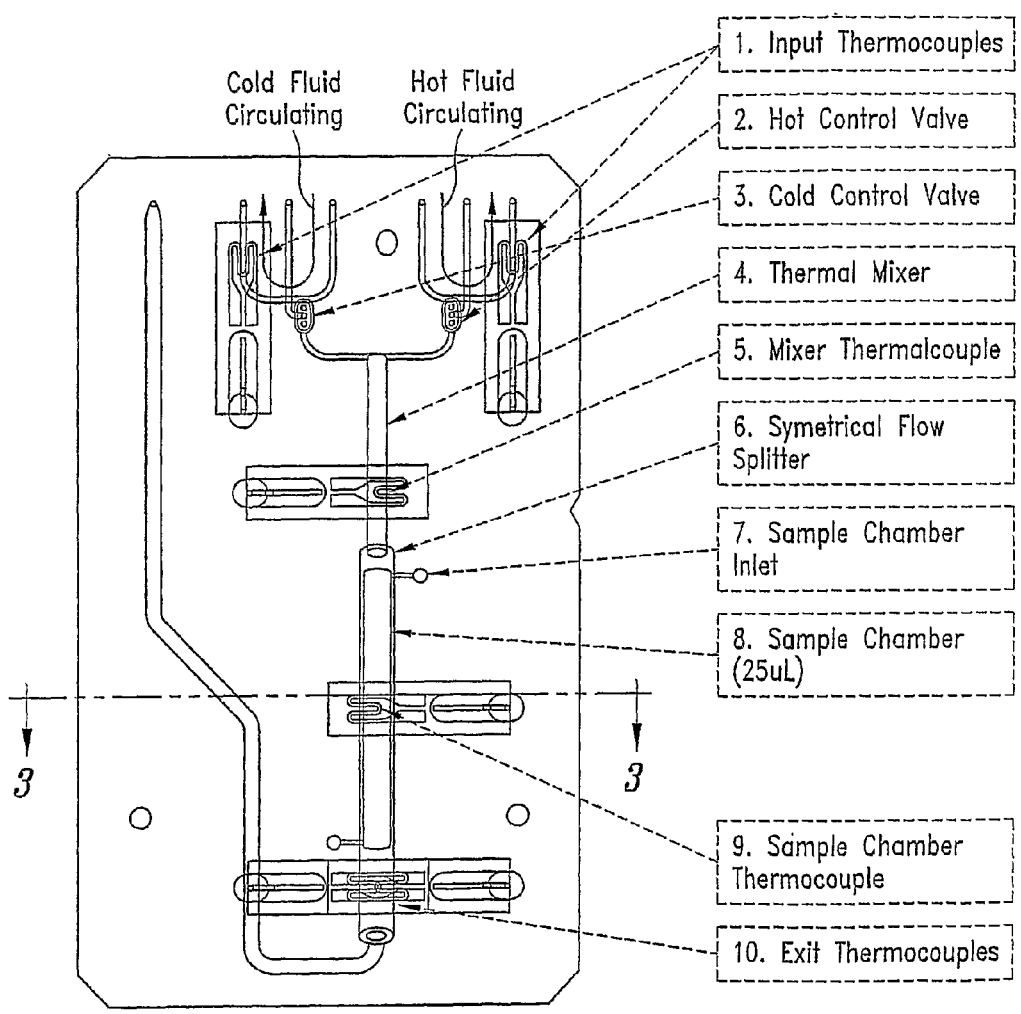
FIG. 14: A plan view of one embodiment of a microfluidic device of the present invention.

Thermal Cycling Parameters:
High temperature annealing: 10 cycles
Low temperature annealing: 45 cycles
FIG. 7 shows that the crossing threshold (Ct) value for the amplicon DNA containing samples (including those mixed with template DNA) is 10 cycles sooner (28 cycles) than the template DNA samples (38 cycles). Melting curve analysis of these samples (FIG. 8) confirms the formation of a single amplification product (peak at 89 deg C.), save for the unexpected amplification in the NTC sample (#9). The size was of the PCR product was confirmed to be ~300 bp (expected size 309 bp) by agarose gel electrophoresis (FIG. 11).

The utility of this technique was tested with 10000 fold higher concentrations of starting DNA than the previous assay as described below.
Experiment B: High concentration reaction of amplicon DNA only, template DNA only and both amplicon and template DNA mixed.
~1.6×10$^7$ copies (2.3 pg) amplicon DNA
~1.2×10$^7$ copies (67.6 pg) target DNA Sample numbering and thermal cycling parameters are the same as in experiment A. In contrast to the previous two experiments (A and B), in real life applications the concentration of amplicon contaminating a PCR reaction will usually be tiny compared to the amount of target DNA. Thus in practice detection of amplicon contamination will require more than 10 cycles of high temperature annealing cycling before switching to the lower temperature annealing cycling.

The following experiment (C) was performed to determine whether a small number of amplicons can be detected in the presence of much higher concentrations of target DNA. The number of cycles of high temperature annealing was increased to 40, followed by 35 cycles of low temperature annealing.
Experiment C: Low concentration of amplicon DNA only, high concentration of target DNA only, and mixture of low amplicon and high target DNA.
~1600 copies (0.23 fg) amplicon DNA
~1.2×10$^7$ copies (67.6 pg) target DNA
Sample Set Up:

| Sample # | |
|---|---|
| 1 | Amplicon (−control) |
| 2 | Amplicon (−control) |
| 3 | Both (+/−control) |
| 4 | Both (+/−control) |
| 5 | Target (+control) |
| 6 | Target (+control) |
| 7 | NTC |
| 8 | NTC |

Thermal Cycling Parameters:
High temperature annealing: 40 cycles
Low temperature annealing: 35 cycles It is clear from this experiment that only samples that contain amplicon amplify during high temperature annealing cycling (FIG. 12), whereas reaction mixes with target DNA are only amplified during the subsequent low temperature annealing cycling phase (FIG. 13) of the 2T-TA PCR. Melting curve data for these samples (peak at 89 deg C.) were very similar to results shown in FIGS. 8 and 10.

SUMMARY

The present invention discloses a method to perform PCR reactions with one set of primers comprising sequence elements that are complementary to the target sequence and comprising sequence elements that serve as tagging sequences. By conducting amplification reactions at different temperatures, the presence of contaminations arising from amplification products of previous reactions can be determined, improving reliability of the reaction and reducing the need for control reactions and reproduction of reactions.

The invention claimed is:
1. Method to amplify nucleic acid sequence, comprising the steps of
   selecting a forward primer comprising a complementary sequence element B that is complementary to a sequence element on said nucleic acid sequence and hybridizes to said nucleic acid sequence, and said forward primer comprising a sequence element A that is not complementary to said nucleic acid sequence and situated upstream of the said complementary primer sequence element, the difference between the annealing temperatures on their respective complementary DNA sequences of the B element and the A and B element together, respectively, being greater than 5 degree Celsius, and
   selecting a reverse primer comprising a complementary sequence element B that is reverse complementary to a different sequence element downstream on said nucleic acid sequence than the forward primer and hybridizes to the complementary strand of said nucleic acid sequence, and said reverse primer comprising a sequence element A that is not complementary to said nucleic acid sequence and situated upstream of the said complementary primer sequence element, the difference between the annealing temperatures on their respective complementary DNA sequences of the B element and the A and B element together, respectively, being greater than 5 degree Celsius, and
   conducting a contamination detection reaction comprising one or several annealing steps followed by one or several polymerisation steps, where the forward and reverse primers are brought into contact with the DNA that is to be amplified in the presence of thermostable DNA polymerase, buffer, and deoxyribonucleotides commonly used in polymerase chain reactions, and an annealing temperature for the annealing steps is selected at which annealing temperature the A and B sequence will anneal to and form stable double helical structures with its complementary DNA sequence but the B sequence element alone will not anneal and form stable double helical structures with its complementary sequence, and conducting a target amplification reaction comprising one or several annealing steps followed by one or several polymerisation steps, where the forward and reverse primers are brought into contact with the DNA that is to be amplified in the presence of thermostable DNA polymerase, buffer, deoxynucleotides and all ingredients commonly used in polymerase chain reactions, and an annealing temperature for the annealing steps is selected at which annealing temperature the B sequence element alone will anneal and form stable double helical structures with its complementary sequence, and determining the absence or presence of a contamination with amplicon from previous polymerase chain amplification reactions with the forward and reverse primers by the absence or presence, respectively, of amplification product after the contamination detection reaction.

2. Method according to claim 1, where the primers are oligodeoxyribonucleotide primers.

3. Method according to claim 1 or 2, where the contamination detection reaction is conducted prior to the target amplification reaction and both reactions are conducted in sequence in the same vessel.

4. Method according to claim 1 or 2, where the contamination detection reaction is conducted in parallel to the target amplification reaction and/or wherein the amount of target DNA present before amplification is determined.

5. Method according to claim 1 wherein the complementary sequence in element B is at least 70% complementary to said sequence element on said nucleic acid sequence.

6. Method according to claim 1 wherein the complementary sequence in element B is fully complementary to the sequence element in the nucleic acid sequence.

7. Method as defined in claim 1 wherein instead of using said reverse primer, a reverse primer is used that comprises an element B, but does not comprise an element A which is complementary to sequence element on the nucleic acid sequence, and wherein in both the contamination detection reaction and the target amplification reaction the reverse primer anneals and forms a stable double helical structure with its complementary sequence.

8. Method according to claim 1 wherein additional primer pairs are used in the contamination detection reaction, the additional primer pairs optionally being complementary to the A elements.

9. Method according to claim 1 wherein the primers defined in claim 1 are labeled with a label, and optionally additional primer pairs are used in the contamination detection reaction, the additional primer pairs optionally being complementary to the A elements and are labeled with a different label than said primers defined in claim 1.

10. Method according to claim 1 wherein at least one A element comprises modified nucleotides PNA or LNA which have a higher free binding energy than normal nucleotides and/or the contamination detection reaction mixture comprises a DNA sequence specific or non-specific binding molecule which binds at least one A element, and thereby increases the annealing temperature of the primers and/or at least one A element has a sequence which forms a hairpin at the annealing temperature of the target amplification reaction, but which does not form a hairpin at the higher annealing temperature of the contamination detection reaction.

11. Method according to claim 1 wherein the sequence which is amplified in the target amplification reaction is:—expressed, and/or—incorporated into a vector, which is optionally replicated, and then optionally expressed, and/or —sequenced.

* * * * *